United States Patent [19]

King

[11] Patent Number: 5,475,222
[45] Date of Patent: Dec. 12, 1995

[54] RUGGEDIZED GAS DETECTOR

[75] Inventor: John D. King, Roseville, Minn.

[73] Assignee: Detector Electronics Corporation, Minneapolis, Minn.

[21] Appl. No.: 349,931

[22] Filed: Dec. 5, 1994

[51] Int. Cl.⁶ ............................ G01N 21/61; G01N 21/17
[52] U.S. Cl. .......................................... 250/343; 250/338.5
[58] Field of Search ................................. 250/338.5, 343, 250/353

[56] References Cited

U.S. PATENT DOCUMENTS

| | | |
|---|---|---|
| 2,468,740 | 5/1949 | Else . |
| 3,417,392 | 12/1968 | Hansen et al. . |
| 3,555,532 | 10/1969 | White et al. . |
| 3,796,887 | 3/1974 | Vincent et al. . |
| 3,861,809 | 1/1975 | Hall, Jr. . |
| 4,124,298 | 11/1978 | Steele . |
| 4,445,359 | 5/1984 | Smith ................................. 250/343 X |
| 4,549,080 | 10/1985 | Baskins et al. ........................ 250/343 |
| 4,560,873 | 12/1985 | McGowan et al. . |
| 4,709,150 | 11/1987 | Burough et al. . |
| 4,889,992 | 12/1989 | Hoberman .............................. 250/343 |
| 5,026,992 | 6/1991 | Wong . |
| 5,163,332 | 11/1992 | Wong . |
| 5,340,986 | 8/1994 | Wong . |
| 5,341,214 | 8/1994 | Wong . |

FOREIGN PATENT DOCUMENTS 60-257347 12/1985 Japan ..................................... 250/343

*Primary Examiner*—Carolyn E. Fields
*Assistant Examiner*—Edward J. Glick
*Attorney, Agent, or Firm*—Palmatier, Sjoquist & Helget

[57] ABSTRACT

A ruggedized gas detector having two or more perforated concentric cylinders and having a concentric screen inside the innermost cylinder. A pair of perforated tubes are positioned inside the perforated screen, and an infrared light source is placed adjacent one end of one of the tubes and an infrared sensor is placed adjacent the other tube. A pair of inclined mirrors are positioned adjacent the respective other ends of the two tubes, and an optical light path is created from the IR source through a first tube, reflected by the mirrors to a return optical path through the second tube and ultimately to the IR sensor.

10 Claims, 2 Drawing Sheets

5,475,222

RUGGEDIZED GAS DETECTOR

BACKGROUND OF THE INVENTION

The present invention relates to a gas detector for measuring the concentrations and presence of unwanted or combustible gases so that an alarm can be given when excessive concentrations of such gases are measured. More particularly, the invention relates to a ruggedized construction for a gas detector which houses a gas chamber and an infrared source and sensor for directing infrared radiation through the chamber to the sensor.

Infrared gas sensors have been widely used in the prior art for either detecting the presence of a gas or measuring the concentration of a gas in a particular environment. These devices use the principle that various gases exhibit substantial absorption at specific wavelengths in the infrared radiation spectrum. If an infrared source is positioned at some spatial distance from an infrared sensor, the amount of infrared energy at specific wavelengths which is absorbed between the source and the sensor provides a measure of particular gas concentrations in the intervening space. The infrared wavelength isolation is typically provided by utilizing narrow band infrared transmission filters which block all wavelengths outside of a predefined wavelength. The predefined wavelength is chosen to be a known wavelength which is absorbed by the particular gas which is being analyzed.

Gas detectors of the general type relating to this invention are particularly useful in detecting gas concentrations which are the byproduct of fires; and therefore, such devices become useful as fire detectors. They offer the advantages of relatively fast response, relatively high stability and sensitivity, and being capable of implementation in a simple structure. These advantages are particularly useful in designing gas detectors for use in a hostile environment, such as an industrial site. Such environments require a highly reliable and ruggedized construction wherein the gas detector may be easily maintained and capable of withstanding physical and environmental abuse. A number of different constructions for gas analyzers of the general type related to this invention are found in the prior art. For example, U.S. Pat. No. 5,341,214, issued Aug. 23, 1994, discloses a gas analyzer having a single infrared source and two detectors spaced apart in a chamber wherein the interior walls of the chamber reflect the radiation. U.S. Pat. No. 5,163,332, issued Nov. 17, 1992, discloses an infrared light source and detector separated at either end of an elongate chamber wherein the chamber has a plurality of openings to permit gas permeation into the chamber. U.S. Pat. No. 4,709,150, issued Nov. 24, 1987, discloses a similar type of gas analyzer wherein the chamber has a porous tube surrounding an enclosed column of air, the porous tube having openings sized to permit gas diffusion through the tube. U.S. Pat. No. 4,560,873, issued Dec. 24, 1985, discloses a combustion gas analyzer with an elongate probe for inserting into a flue or gas stack. An optical path is reflected through the elongate probe via a light source and a photocell to detect the presence of gas in the probe.

There is a need for a gas detector of the general type disclosed in the foregoing patents having an extremely rugged construction for permitting reliable operation in an industrial setting, and wherein the measurement chamber is protected from water and dust accumulation.

SUMMARY OF THE INVENTION

The present invention comprises a ruggedized gas detector having a plurality of concentric cylindrical components surrounding a pair of interior gas cells which comprise a pair of tubular members. An infrared (IR) source and detector are adjacently positioned near an end of the respective tubular members, and the opposite end of the tubular members has a pair of reflective mirrors. The IR source is directed through one of the tubular members and is reflected via the mirrors backwardly through the other tubular member where it is received by the IR sensor. Suitable openings are provided in all of the concentrically positioned cylinders and tubular members to permit the permeation of gas therethrough.

It is the principal object and advantage of the present invention to provide a ruggedized gas detector utilizing fixedly mounted concentric tubes for protecting interior gas chambers and an IR source and detector.

It is another object of the present invention to provide a ruggedized gas detector having exterior metallic guards for shielding the interior components from water and dust accumulations.

The foregoing and other objects and advantages of the invention will become apparent from the following specification and claims, and with reference to the appended drawings.

DESCRIPTION OF THE PREFERRED EMBODIMENT

Figure 1:
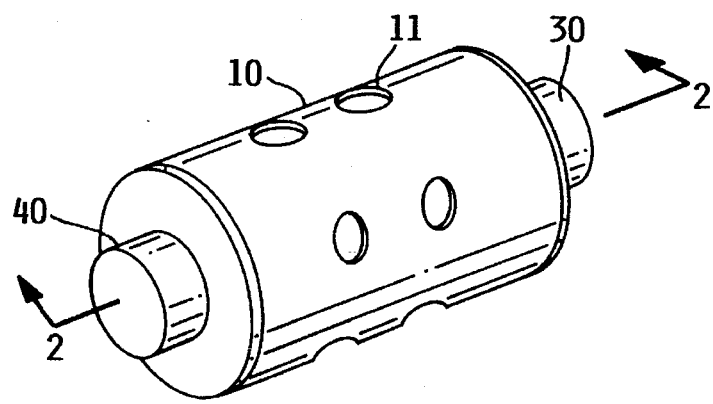
FIG. 1 shows an isometric view of the present invention.

FIG. 1 shows an isometric view of the apparatus, wherein an outer perforated cylinder 10 surrounds the entire apparatus and serves as a water and dust guard. One end of the cylinder 10 is enclosed and affixed to a housing 30 which projects outwardly from the end of the cylinder. The other end of the cylinder 10 is enclosed and affixed to a housing 40 which projects from the other end of the cylinder. The cylinder 10 has a plurality of openings 11 which are uniformly arranged about the circumference of the cylinder and along the length of the cylinder.

Figure 2:
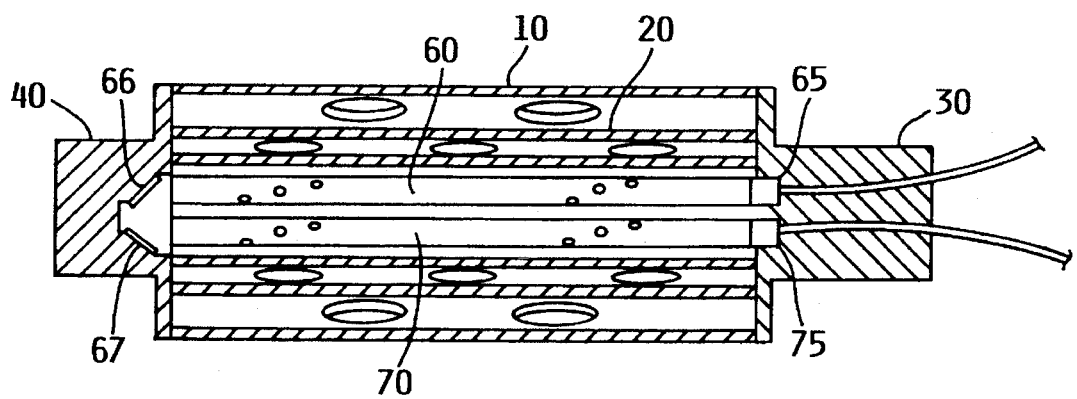
FIG. 2 shows a cross-section view taken along an elongate axis of the device of FIG. 1.

FIG. 2 shows a cross-section view of the apparatus of FIG. 1, taken along the elongate axis of cylinder 10 and housings 30, 40. An interior cylinder 20 is concentrically positioned inside of cylinder 10, and cylinder 20 has a plurality of openings which are uniformly arranged along its length. The openings in cylinder 20 are misaligned relative to the openings in cylinder 10 so that no single direct path exists from the exterior of the apparatus to the interior of cylinder 20.

A pair of tubes 60, 70 are confined between housings 30, 40 and are centrally positioned inside of cylinder 20. The tubes 60, 70 form the optical path for the invention. A light source 65 is affixed in housing 30 and is positioned adjacent the end of tube 60. A mirror 66 is positioned adjacent the other end of tube 60 and is arranged at an angle of approximately 45°, so as to reflect light from light source 65 substantially normally to the axis of tube 60. A second tube 70 is also affixed between housings 30, 40 and a light sensor 75 is affixed within housing 30 and adjacent one end of tube 70. A mirror 67 is positioned adjacent the other end of tube 70 and is also aligned at an angle of approximately 45°. An optical path is formed from light source 65 through tube 60, reflected by mirrors 66, 67 and passing through tube 70 to the light sensor 75. Each of the tubes 60, 70 have a plurality of openings therethrough, generally misaligned relative to any of the openings in cylinder 20.

A cylindrical screen 50 is confined between housings 30, 40 and outside of tubes 60, 70. Screen 50 is comprised of a fine fiberglass mesh coated with a material such as polytetrafluoroethylene, or other water repellant material, and screen 50 has permeable openings therethrough which are sufficiently large so as to freely permit the flow of gas but sufficiently small so as to prevent any water droplets from passing through the screen 50. Water droplets which may collect on the exterior surface of screen 50 will, therefore, drop downwardly onto the cylinder 20, and through the openings of the cylinder 20 to cylinder 10, and outwardly therefrom.

Figure 3:
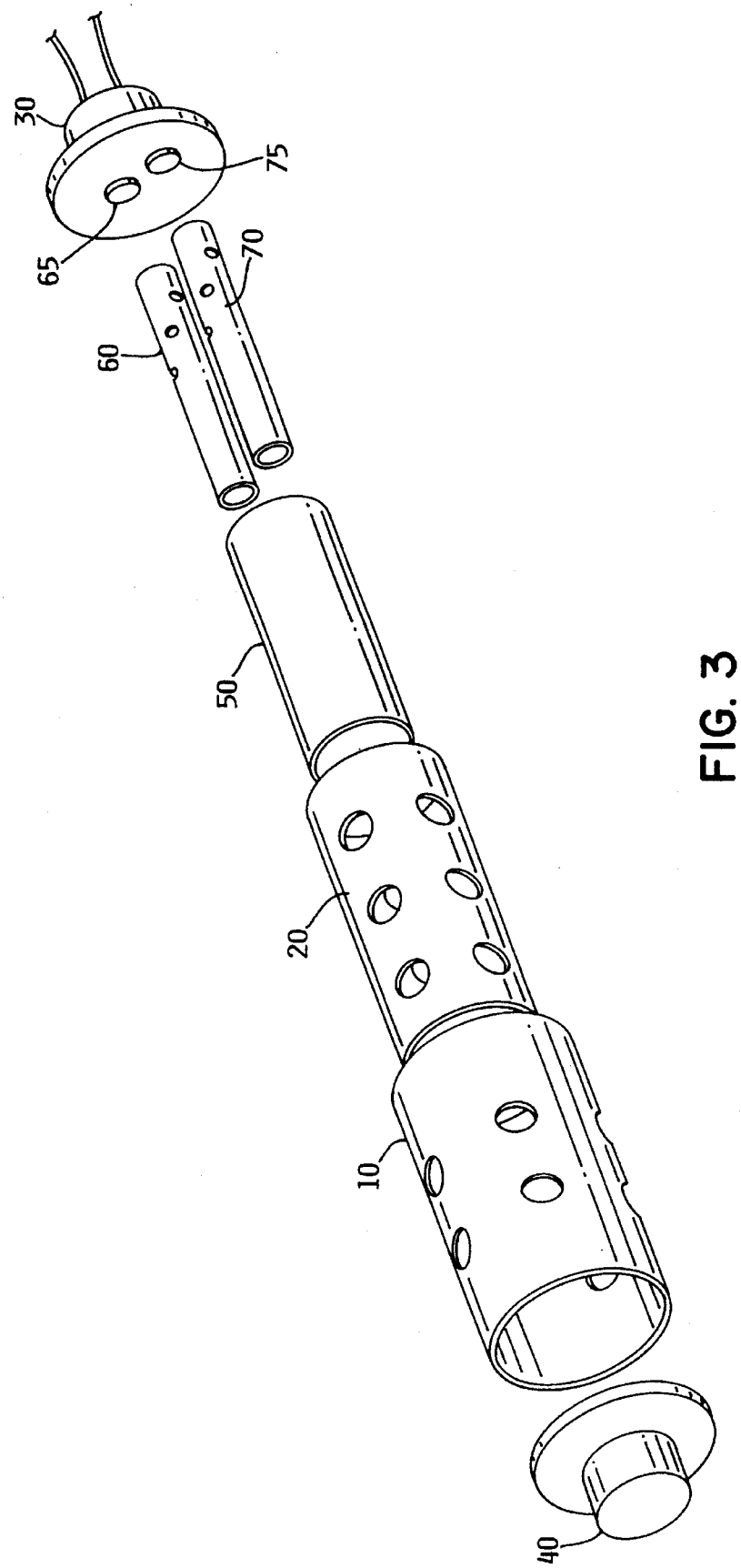
FIG. 3 shows an exploded isometric view illustrating the components of the invention.

FIG. 3 shows an exploded view of the apparatus, illustrating each of the components in isometric view. The outer perforated cylinder 10 is preferably made of stainless steel or like material and may have a large number of perforated openings therethrough. It may have any convenient axial length, for example, a length of approximately 6–12 inches. The inner perforated cylinder 20 is made from similar material having the same axial length as cylinder 10, and it may have many perforated openings. The openings through cylinder 20 should be positioned so as not to be alignable with any of the openings in cylinder 10. Cylinder 50 is formed from a fine mesh material and has the same axial length as cylinders 10 and 20. Cylinder 50 forms a hydrophopic screen which permits the flow of gas therethrough but prevents the flow of water molecules therethrough. Tubes 60 and 70 are identically sized and sufficiently small so as to fit through cylinder 50 in side-by-side arrangement. Tubes 60 and 70 may each have a plurality of perforations therethrough so as to permit the free flow of gas through and into the interior of tubes 60 and 70. Tubes 60 and 70 are of the same axial length as cylinders 50, 20, 10, and are fixedly housed along the inside of cylinder 50. All of cylinders 10, 20, 50, and tubes 60, 70 are fixedly held between housings 30 and 40. Mirrors 66, 67 are affixed in housing 40 in a position which is adjacent the respective open ends of tubes 60, 70. IR source and sensor 65, 75 are affixed in housing 30 and are positioned adjacent the respective open ends of tubes 60, 70. The wires for sending and receiving signals to the IR source 30 and IR sensor 75 extend through housing 30 to the exterior of the apparatus.

The precise number of perforated openings which may be made through the outer cylinder 10, inner cylinder 20, and tubes 60 and 70, is Selected on the basis of balancing several effects. On the one hand, the greater the number of perforated openings, the faster will be the response of the device to the detection of gas concentrations. On the other hand, the fewer the number of perforated openings, the better will be the protection from water and dirt penetration for the components at the interior of the device. In one preferred embodiment which has been satisfactorily tested, 65 perforated openings were made through the outer cylinder 10, and 48 openings were made through the inner cylinder 20. Forty openings were made through each of the tubes 60 and 70. The perforated openings through cylinders 10 and 20 were constructed so as to be misaligned relative to each other and so that no direct path for water or dirt accumulation could be achieved along any radial line emanating from the axis of the device.

In operation, the apparatus is placed into an environment wherein the content and/or concentration of particular gases are desired to be monitored. Air and gas may pass freely through all of the respective perforated openings of the exterior cylinders and may permeate through the perforated screen 50 and the interior tubes 60, 70. The IR source, preferably used in conjunction with one or more narrow band filters, continually directs IR energy at a particular wavelength into the end of tube 60. This radiation is reflected back to IR sensor 75 via the optical paths comprising tubes 60 and 70 and the mirrored surfaces of mirror 66, 67. When an amount of gas begins to accumulate in the tubes 60, 70, a certain portion of the IR radiant energy is absorbed by the gas, thereby reducing the signal strength received by IR sensor 75. IR sensor 75 is typically connected to some form of threshold and trigger circuit so that when the signal strength received by IR sensor 75 decreases below a predetermined threshold, an alarm signal may be generated. This alarm signal is indicative of the presence of the gas being monitored in sufficient quantities as to exceed the predetermined threshold.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. An apparatus for detecting gas concentrations in a chamber having an optical path therethrough, according to the principle of gas absorption of predetermined infrared wavelengths, comprising:

a) a first housing having an infrared source and an infrared detector mounted therein;

b) a second housing having infrared-reflective surfaces therein;

c) a pair of perforated tubular chambers mounted between said first and second housings, one of said chambers aligned between said infrared source and a reflective surface, and the other of said chambers aligned between said infrared detector and a reflective surface, whereby an optical path is formed from said source to said detector;

d) an air-permeable screen enclosing said pair of perforated chambers and mounted between said first and second housings;

e) a first perforated cylinder concentrically positioned about said screen and mounted between said first and second housings; and f) a second perforated cylinder concentrically positioned about said first perforated cylinder and mounted between said first and second housings.

2. The apparatus of claim 1, wherein said first and second perforated cylinders are mutually aligned so that no direct path exists through perforations of the respective cylinders.

3. The apparatus of claim 2, wherein said first and second cylinders are constructed of metal material.

4. The apparatus of claim 3, wherein said screen is constructed of polytetrafluoroethylene material.

5. A gas detector apparatus utilizing an infrared optical path, comprising:

a) a first housing having an infrared source and an infrared detector;

b) a second housing having infrared-reflective surfaces, said second housing fixedly positioned relative to said first housing whereby an optical path is formed from said infrared source to said infrared detector by reflection via said infrared-reflective surfaces;

c) a first perforated cylinder mounted between said first and second housings;

d) a second perforated cylinder concentrically positioned inside said first perforated cylinder; and e) an air-permeable cylindrical screen concentrically positioned inside said second perforated cylinder and about said optical path.

6. The apparatus of claim 5, further comprising a first perforated tubular member inside said cylindrical screen and surrounding the portion of said optical path formed between said infrared source and one of said infrared-reflective surfaces.

7. The apparatus of claim 6, further comprising a second perforated tubular member inside said screen and surrounding the portion of said optical path between said infrared detector and another of said infrared-reflective surfaces.

8. The apparatus of claim 7, wherein said first and second perforated cylinders are respectively concentrically positioned about an axis, and respective perforations in said cylinders are aligned so that no direct radial path from said axis passes through perforations in both said first and second perforated cylinders.

9. The apparatus of claim 8, wherein said air-permeable cylindrical screen further comprises a fine mesh having openings sufficiently small as to prevent water droplets from passing therethrough.

10. The apparatus of claim 9, wherein said air-permeable cylindrical screen is coated with polytetrafluoroethylene material.

* * * * *